＝

US008277835B2

(12) United States Patent
Boehm et al.

(10) Patent No.: US 8,277,835 B2
(45) Date of Patent: Oct. 2, 2012

(54) NUTRITIONAL COMPOSITION COMPRISING IMMUNOGLOBULINS AND OLIGOSACCHARIDES

(75) Inventors: Günther Boehm, Echzell (DE); Laura M'Rabet, Amersfoort (NL); Bernd Stahl, Rosbach-Rodheim (DE); Johan Garssen, Nieuwegein (NL); Antony William Scammell, Adelaide (AU); Raymonde Peter Peeters, Adelaide (AU)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 11/574,123

(22) PCT Filed: Aug. 24, 2005

(86) PCT No.: PCT/NL2005/000612
§ 371 (c)(1),
(2), (4) Date: Feb. 22, 2007

(87) PCT Pub. No.: WO2006/022543
PCT Pub. Date: Mar. 2, 2006

(65) Prior Publication Data
US 2007/0274983 A1 Nov. 29, 2007

(30) Foreign Application Priority Data
Aug. 24, 2004 (EP) .................................. 04077394

(51) Int. Cl.
A61K 47/00 (2006.01)
A01N 43/04 (2006.01)
A23D 9/00 (2006.01)
A23C 9/154 (2006.01)
A23J 1/00 (2006.01)
A23G 3/00 (2006.01)

(52) U.S. Cl. ........ 424/439; 426/658; 426/656; 426/601; 426/580; 514/54

(58) Field of Classification Search ................... None
See application file for complete search history.

(56) References Cited

U.S. PATENT DOCUMENTS

| | | | |
|---|---|---|---|
| 4,661,345 A | 4/1987 | Tuomanen | |
| 4,800,078 A * | 1/1989 | Prince et al. | 424/159.1 |
| 4,919,961 A | 4/1990 | Lundblad | |
| 5,792,754 A * | 8/1998 | Green et al. | 514/60 |
| 5,902,617 A * | 5/1999 | Pabst | 426/61 |
| 5,922,344 A | 7/1999 | Hilty et al. | |
| 6,146,670 A | 11/2000 | Prieto et al. | |
| 6,863,918 B2 * | 3/2005 | Bindels et al. | 426/590 |
| 7,794,746 B2 | 9/2010 | Gibson et al. | |
| 2003/0022863 A1 | 1/2003 | Stahl et al. | |
| 2003/0072865 A1 | 4/2003 | Bindels et al. | |
| 2004/0062758 A1* | 4/2004 | Mayra-Makinen et al. | 424/93.45 |
| 2004/0072791 A1 | 4/2004 | Kunz et al. | |
| 2004/0131659 A1 | 7/2004 | Gibson et al. | |
| 2008/0124323 A1 | 5/2008 | Boehm | |

FOREIGN PATENT DOCUMENTS

| | | |
|---|---|---|
| AU | 766429 B2 | 10/2003 |
| EP | 0 126 043 | 11/1984 |
| EP | 0 272 095 | 6/1988 |
| EP | 0 808 173 A | 11/1997 |
| EP | 0 756 828 B1 | 11/1998 |
| EP | 1 254 664 A | 11/2002 |
| NZ | 522916 A | 3/2004 |
| WO | WO 92/02817 | 2/1992 |
| WO | WO 96/31186 | 10/1996 |
| WO | WO 96/40169 | 12/1996 |
| WO | WO 00/08948 | 2/2000 |
| WO | WO 00/42868 * | 7/2000 |
| WO | WO 01/41581 A1 | 6/2001 |
| WO | WO 01/97817 A1 | 12/2001 |
| WO | WO 02/02105 A1 | 1/2002 |
| WO | WO 03/026567 A2 | 4/2003 |
| WO | WO 03/028738 A2 | 4/2003 |
| WO | WO 2004/052121 A | 6/2004 |
| WO | WO 2006/018314 A2 | 2/2006 |
| WO | WO 2006/022542 A1 | 3/2006 |

OTHER PUBLICATIONS

Food and Nutrition Bulletin (The United Nations University Press) vol. 17, No. 4, Dec. 1996 (Constituents of Breast Milk and Protective Effect of Breast Milk against Infection).*
Lowry et al (Infant Formulas—An update obtained from http://www.hini.org/HINI/infform.htm) 2001—retrieved online Apr. 28, 2008.*
Niness et al The Journal of Nutrition 129:1420S-1406S, 1999.*
Hemming et al Clinical and Diagnostic Lab. Immunol. Sep. 2001 p. 859-863.*
Taylor et al. Clin Exp Immunol 1992 vol. 90:357-362.*
Sabchareon et al. Am J Trop Med Hyg 1991 vol. 45:297-308.*
Boehm et al. Arch Dis Child Fetal Neonatal Ed 2002; 86:F178-F181.*
Definition of Infection—http://www.mercksource.com/pp/us/cns/cns_hl_dorlands_split.jsp?pg=/ppdocs/us/common/dorlands/dorland/four/000053439.htm. Retrieved Jan. 21, 2009.*
Definition of Infection—Online Medical Dictionary http://cancerweb.ncl.ac.uk/cgi-bin/omd?infection. Retrieved Jan. 21, 2009.*
Definition of Infection—American Heritage Dictionary (http://www.bartleby.com/61/70/I0127000.html. Retrieved Jan. 21, 2009.*
Definition of Infection—Stedman's Online Medical Dictionary (http://www.stedmans.com/section.cfm/45.Retrieved Jan. 21, 2009.*
Upper Respiratory Tract Infections—http://www.clevelandclinicmeded.com/medicalpubs/diseasemanagement/infectious-disease/upper-respiratory-tract-infection/, retrieved Jan. 21, 2009.*
Hatakka et al BMJ;322;1-5, 2001.*

(Continued)

Primary Examiner — Oluwatosin Ogunbiyi
(74) Attorney, Agent, or Firm — Gilberto M. Villacorta; Sunit Talapatra; Foley & Lardner LLP

(57) ABSTRACT

The present invention provides a method and composition for the treatment and/or prevention of infection, said method comprising orally administering a composition to a mammal, said composition comprising a galactose containing indigestible oligosaccharide and immunoglobulin from the milk or colostrum of hyperimmunized cows.

9 Claims, No Drawings

OTHER PUBLICATIONS

B. Anderson et al., "Inhibition of Attachment of *Streptococcus pneumoniae* and *Haemophilus influenzae* by Human Milk and Receptor Oligosaccharides", The Journal of Infectious Diseases, vol. 153, No. 2, (1986).

D.S. Newburg et al., "Carbohydrates in Milks: Analysis, Quantities, and Significance" Handbook of Milk Composition, New York: Academic Press, 1995, Chapter 4.

J. Charlwood et al, "A Detailed Analysis of Neutral and Acidic Carbohydrates in Human Milk," Analytical Biochemistry, vol. 273, issue 2, 1999.

A. Prentice, "Constituents of human milk", Food and Nutrition Bulletin, vol. 17, No. 4 (1996).

A. Sinha et al, "Reduced Risk of Neonatal Respirator Infections Among Breasted Girls but Not Boys", Pediatrics, vol. 112, No. 4, 2003.

C.R. Pullen et al., "Breast-feeding and respirator syncytial virus infection", British Medical Journal, vol. 281 (1980).

M A P S Downham et al, "Breast-feeding protects against respiratory syncytial virus infections", British Medical Journal, vo. 2., 1976.

E. Tuomanen et al., "Receptor Analogs and Monoclonal Antibodies that Inhibit Adherence to *Bordetella pertusis* to Human Ciliated Respiratory Epithelian Cells", J. Exp. Med. vol. 168 (1988).

M. Rivero et al, "P1121 Effect of a New Infant Formulae Enriched Prebiotics, Probiotics, Nucleotides and LC-Pufa's on Infants Recovery after an Infection" [abstracts], Journal of Pediatric Gastroenterology and Nutrition, vol. 39, supplement 1, 2004.

Flexnews, "Friesland Foods Domo Further Expands Production Capacity", download Jan. 21, 2008 from http://www.flex=news.food.com/pages/8170/Friesland'friesland_foods_dome_furhter_expands_production_capacity.html.

J.M. Saavedra et al., "Human studies with probiotics and prebiotics: clinical implications", British Journal of Nutrition, vol. 87, Suppl. 2 (2002).

Elix' or (Milupa Friedrichsdorf 29$^{th}$ of Jun. 1998).

Elix' or Galacto-oligosaccharides—A natural ingredient for functional foods.

Mar. 31, 2007 Frank Fox Declaration Elix' or brochure 1996.

Elix' or Galacto-oligosaccharides—for Innovative Foods.

E. Birch et al, "A randomized controlled trial of long-chain polyunsaturated fatty acid supplementation of formula in term infants weaning at 6 wk of age", American Journal of Clinical Nutrition, vol. 75, No. 3, (2002).

S.E. Carlson et al., "N-Acetylneuraminic acid concentrations in human milk oligosaccharides and glycoproteins during lactation" Am. J. Clin.Nurt., vol. 41(4), 1985.

Gibson, et al., "Dietary Modulation of the Human Colonic Microbiota: Introducing the Concept of Prebiotic," *J Nutr.*, Jun. 1995, vol. 125, No. 6, pp. 1401, 1405.

Devereux, H.M. et al., "Consumer Acceptability of Low Fat Foods Containing Inulin and Oligofructose", Journal of Food Science, 2006, vol. 68, Issue 5, pp. 1850-1854 (Abstract Only).

Urashima, Tadasu et al., "Oligosaccharides of Milk and Colstrum in Non-Human Mammals," Glycoconjugate Journal, 2001, vol. 18, pp. 357-371.

Yolken, Robert H. et al., "Antibody to Human Rotavirus in Cow's Milk," The New England Journal of Medicine, 1985, vol. 312, No. 10, pp. 605-610.

McIntosh, K., "Respiratory Syncytial Virus," Viral Infections of Humans: Epidemiology and Control, 1997, Chapter 23, pp. 691-711.

International Search Report dated Jan. 20, 2006, PCT/NL2005/000612.

"Diagnosing RSV" from the RSV Info Center [online], [retrieved Aug. 11, 2010]. Retrieved from the internet http://www.rsvinfo.com/diagnosing/diagnosing.html. Published on Feb. 20, 1999.

"Respiratory syncytial virus(RSV)" MedlinePlus Medical Encyclopedia [online], [retrieved Aug. 11, 2010]. Retrieved from the internet http://www.nlm.nih.gov/medlineplus/ency/articie/001564.htm. Published on Jun. 17, 2001.

"Viral Upper Respiratory Infections" from the Galen Medical Group [online], [retrieved Aug. 9, 2010]. Retrieved from the internet http://www.galenmedical.com/downloadsNiralinfections824.pdf. Published on May 24, 2006.

Gibson, G.R., Rabiu, B., Rycroft, C.E., Rastall, RA (2004) "Trans-Galactooligosaccharides as Prebiotics" in the Handbook of Functional Dairy Products. Edited by Colette Shortt and John O'Brien. Published by CRC Press.

Kayser,F.H. (1992) "Changes in the spectrum of organisms causing respiratory tract infections: a review," Postgrad Med J, vol. 68 (Suppl. 3), 1992, pp. S17-S23.

\* cited by examiner

NUTRITIONAL COMPOSITION COMPRISING IMMUNOGLOBULINS AND OLIGOSACCHARIDES

FIELD OF THE INVENTION

The present invention provides a method for the prevention and/or treatment of intestinal and/or respiratory tract infections, said method comprising the administration of a nutritional composition containing antibodies and indigestible oligosaccharides.

BACKGROUND OF THE INVENTION

The respiratory tract and intestinal tract are common sites for infection by pathogens. Despite the host organism often having a functioning immune system, the respiratory and intestinal tract frequently become infected because they are in direct contact with the physical environment and are exposed to pathogenic microorganisms (such as viruses, bacteria, protozoa, fungi, etc.) that can be transmitted e.g. by touch, in the air and via food. There are many microorganisms that cause illness in infants and other individuals. For individuals whose immune systems are compromised the risk of infection and serious illness is even higher.

Respiratory syncytial virus (RSV) is the leading cause of serious lower respiratory tract disease in infants and children. Primary RSV infection occurs most often in children from 6 weeks to 2 years of age. RSV is estimated to cause as much as 75% of all childhood bronchiolitis and up to 40% of all pediatric pneumonias. Children at increased risk from RSV infection include preterm infants and children with bronchopulmonary dysplasia, congenital heart disease, congenital or acquired immunodeficiency and cystic fibrosis. The fatality rate in infants with heart or lung disease who are hospitalized with RSV infection is 3%-4%. Treatment options for established RSV disease are limited. Severe RSV disease of the lower respiratory tract often requires considerable supportive care, including administration of humidified oxygen and respiratory assistance.

Epidemiology studies also show that the incidence of asthma and allergy in children up to 12 years of age is considerably higher in children who have been hospitalized as infants with RSV infection.

Acute otitis media (AOM) is the most frequent diagnosis in physician offices among children 1-4 years of age. There is strong correlation between the presence of virus in the nasopharynx and the occurrence of otitis media; using sensitive molecular testing methods (eg PCR), respiratory viruses have been detected in up to 90% of cases. RSV, adenoviruses and influenza virus are most frequently seen; RSV accounts for 10-70% of viral isolations from middle ear fluid. In a study of infants aged 2-24 months with bronchiolitis, 86% had AOM; RSV was isolated from 71% of patients. In a majority of cases, viral infection of the nasopharynx and distal tubes cause Eustachian tube dysfunction, resulting in transient negative middle ear pressure, thus facilitating secondary viral or bacterial otitis media. The most common bacteria involved in the mixed RSV-bacterial infections are *Streptococcus pneumoniae* and *Haemophilus influenzae*. Further, there is evidence that enhanced synthesis of proinflammatory cytokines and cell adhesion molecules in the middle ear infected with RSV may contribute to the inflammatory processes in otitis media.

RSV is also very prevalent in the elderly, and along with influenza, a major cause of death, however, there is as yet no vaccine available to prevent death caused by RSV.

Rotavirus infection can cause gastroenteritis. It most often infects infants and young children. In children aged 3 months to 2 years, rotavirus is one of the most common causes of diarrhea, and hospitalisations. Rotavirus leads to outbreaks of diarrhea during the winter months and is particularly a problem in child-care centers and children's hospitals. Almost all children have had a rotavirus infection by the time they are 3 years old. Infected infants may experience a spectrum of symptoms ranging from vomiting, diarrhea, fever, dehydration and pain to more serious long-term complications such as lactose malabsorption, carbohydrate intolerance, early onset of protein intolerance and increased susceptibility to other infections. Rotavirus is a major cause of infant death in countries with poor public health systems.

Prevention of respiratory and intestinal infections has proven difficult, with very few vaccines available to prevent infections of the respiratory or intestinal tract, particularly in relation to RSV and rotavirus. Prevention of RSV infection in infants who are at high risk of death from RSV is attempted by the regular intramuscular injection of a monoclonal antibody. This monoclonal antibody has an effect in reducing the occurrence of serious cases of RSV in at risk children. However, it is highly invasive, very expensive, and only available to a small proportion of people at risk from RSV infection and the ongoing illness that can result.

Infants breast-fed with mother's milk have a reduced occurrence and a reduced severity of respiratory tract and intestinal tract infections. In the art, it is presently believed that this reduced occurrence and severity is partly because mother's milk contains immunoglobulin(s) with virus and/or other microorganism neutralizing activity.

Treatment of intestinal and respiratory infection is often difficult. Most cases are treated with palliative care only. Treatment for rotavirus infection is limited to oral and/or intravenous rehydration. Only a few effective drugs are available for respiratory infection and often treatment requires pulmonary administration of the drug. In young infants this leads to significant stress. Therefore there is a need for further effective agents that preferably can be administered without imposing stress, or with at least decreasing the amount of stress imposed on infants and children.

Some pathogens which gain entry to the body via the intestinal and/or respiratory tract are associated with systemic disease. For example, herpes virus can initially gain entry via the respiratory tract before invading and residing in other parts of the body to cause disease over time.

WO9613271 describes a composition for promoting gastrointestinal health comprises an effective amount of a beneficial human intestinal microorganism and an effective amount of an immunoglobulin composition comprising concentrated immunologically active immunoglobulins. Another composition for restoring and maintaining gastrointestinal health comprises 40-60% by weight of an immunoglobulin composition comprising concentrated immunologically active immunoglobulins and 40-60% by weight of soluble dietary fiber selected from inulin, fructo-oligosaccharides, pectin, guar gum, and mixtures thereof.

SUMMARY OF THE INVENTION

In a multicentre clinical trial, the present inventors have now surprisingly found that enteral administration a nutritional composition containing galactooligosaccharides to infants can be used to reduce the incidence and/or severity of infections, particularly respiratory tract infections. The anti-infective effects have not previously been described for galactose containing soluble dietary fibers such as galactooligosaccharides (GOS).

Additionally, the present inventors have found that galactooligosaccharides stimulate the immune system. These observations have resulted in the hypothesis that the infection reducing properties of galactose containing prebiotic components (for example GOS) is the result of a combination of an improved immune response and a positive stimulation of the intestinal flora.

These insights in the mode of action of galactose containing oligosaccharides have now resulted in the possibility to further improve infant nutrition and have resulted in the development of the present composition and the present methods to reduce infections.

The present invention provides a composition that contains galactose containing prebiotic components and one or more immunoglobulins with activity against one or more pathogenic micro-organisms, such as one or more pathogenic viruses, bacteria, fungi, etc. Preferably the immunoglobulins are obtained from mammalian colostrum or milk, produced by mammals treated with antigens, e.g. cows hyperimmunized against one or more human pathogens.

In particular, the combination of the immune-stimulatory effects of the GOS in combination with the respiratory virus neutralizing effects of the immunoglobulin provide an advantageous combination for the treatment and prevention of respiratory tract infection caused by viruses.

In a further preferred embodiment, the combination of the Bifidobacteria stimulating effect, immune-stimulatory effect of GOS, and virus neutralizing effects of the immunoglobulins is particularly effective in the treatment and/or prevention of intestinal infections, e.g. rotavirus infection.

The oligosaccharides and (one or more) specific immunoglobulins act synergistically. The anti-rotavirus immunoglobulin binds the rotavirus, which is subsequently neutralized by the intestinal immune system.

The oligosaccharides stimulate the growth of Bifidobacterium, which reduces rotavirus infection. Additionally the oligosaccharides stimulate the reestablishment of a normal intestinal flora during and after the rotavirus infection. This reduces the severity and period of diarrhea, as well as the chances for re-infection with a pathogen. Furthermore both ingredients can be combined in infant nutrition, making additional intervention unnecessary.

In a further preferred embodiment, the present invention relates to a combination of one or more immunoglobulins, galactose containing oligosaccharides and acid oligosaccharides. The acid oligosaccharides prevent the adhesion of pathogens to the epithelial cells, resulting in yet a further reduction of infections (both incidence and/or severity of infection and/or reinfections).

In a particular effective embodiment, the present invention provides a composition comprising galactose containing oligosaccharides, immunoglobulin with respiratory virus neutralizing activity, and immunoglobulin with intestinal virus neutralizing activity. The present composition can be easily made by hyperimmunizing cows for both viruses and combining the mammary secretion product with a galactose containing oligosaccharides.

The present compositions are particularly effective in preventing and reducing infection in an infant without the need to inject or administer orally multiple antigens by means of an active vaccine, or to inject monoclonal antibodies. In fact preferably the present composition is orally ingested and can be administered as a food or a pharmaceutical preparation, preferably the present composition is included in food compositions.

DETAILED DESCRIPTION OF PREFFERED EMBODIMENTS

In one aspect the present invention provides a method for the treatment and/or prevention of infection, said method comprising administering a composition comprising: a galactose containing indigestible oligosaccharide containing at least two terminal saccharide units, wherein at least one terminal saccharide unit is selected from the group consisting of glucose and galactose; and at least one terminal saccharide is selected from the group consisting of galactose and fucose; and immunoglobulin having activity against one or more pathogenic microorganisms.

In a further aspect the present invention provides a composition suitable for the treatment and/or prevention of infection or disease comprising a galactose containing indigestible oligosaccharide containing at least two terminal saccharide units, wherein at least one terminal saccharide unit is selected from the group consisting of glucose and galactose; and at least one terminal saccharide is selected from the group consisting of galactose and fucose; and an immunoglobulin having activity against pathogenic microorganisms.

Oligosaccharides

The present invention comprises the administration of a galactose containing indigestible oligosaccharide (GAL-oligo) containing at least two terminal saccharide units, wherein at least one terminal saccharide unit is selected from the group consisting of glucose and galactose; and at least one terminal saccharide is selected from the group consisting of galactose and fucose. Preferably the saccharides of the GAL-oligo are β-linked.

The term "terminal saccharide" refers to a saccharide, which is bound to one other saccharide unit (e.g. galactose, glucose, fructose or fucose). The present GAL-oligo preferably contains not more than 4 terminal saccharides, preferably not more than 2.

The term "indigestible oligosaccharides" as used in the present invention refers to saccharides which are not or only partially digested in the intestine by the action of acids or digestive enzymes present in the human upper digestive tract (small intestine and stomach) but which are fermented by the human intestinal flora.

In a preferred embodiment, the GAL-oligo contains at least one terminal galactose and one selected from at least terminal glucose and one terminal fucose. Even more preferably, the present galactose containing indigestible oligosaccharide comprises at least one terminal galactose and at least one terminal glucose. Preferably the oligosaccharide consists of 2 terminal saccharide units and 2 to 60 saccharide units in total.

Preferably the GAL-oligo is selected from the group consisting of transgalactooligosaccharides, galactooligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalactooligosaccharides ([galactose]$_n$-glucose; wherein n is an integer between 1 and 60, i.e. 2, 3, 4, 5, 6, . . . , 59 ,60; preferably n is selected from 2, 3, 4, 5, 6, 7, 8, 9, or 10). Transgalactooligosaccharides (TOS) are for example sold under the trademark Vivinal™ (Borculo Domo Ingredients, Netherlands). Preferably the saccharides of the transgalactooligosaccharides are β-linked.

The present composition may be in powder or liquid form. The present composition preferably comprises 0.1 to 12 grams of the GAL-oligo per 100 gram dry weight of the composition, preferably between 0.5 and 8 grams, more preferably between 1.0 and 7.5 grams. After reconstitution of the powder in liquid and administration of the liquid formula to the infant, these amounts of GAL-oligo provide the desired effects without causing intestinal discomfort.

Immunoglobulins

The present composition contains at least one immunoglobulin having neutralizing activity against one or more pathogenic microorganisms. The present immunoglobulin preferably has neutralizing activity against one or more viruses, bacteria, protozoa, parasites or prions. In a preferred embodiment the immunoglobulin(s) have virus neutralizing activity.

When referring to "activity" or "neutralizing activity" of an immunoglobulin, or a mixture of immunoglobulins (such as IgG and IgA), reference is made to the ability of the immunoglobulin(s) to bind the pathogen(s) against which the immunoglobulin was raised and reduce it's harmful effects in vivo, particularly to bind the antigens used for immunizing the animal. The activity can be tested using in vitro or in vivo binding assays. A "specific immunoglobulin" or "specific immunoglobulins" neutralizes one pathogenic microorganism (e.g. one virus or viral strain, one bacterial species or strain, etc.), namely the one it/they was/were raised against.

Preferably the composition comprising an immunoglobulin (or a mixture of immunoglobulins) having neutralizing activity against one or more viruses that infect the respiratory tract (i.e. an immunoglobulin having respiratory virus neutralizing activity) and/or an immunoglobulin (or a mixture of immunoglobulins) having neutralizing activity against one or more viruses that infect the intestinal tract (an immunoglobulin having intestinal virus neutralizing activity). More preferably the present composition contains an immunoglobulin (or Ig mixture) capable of neutralizing a virus selected from the group consisting of Myxovirus, Orthomyxokvirus, Rhinovirus, Echoviruses, Coxsackieviruses, Adenovirus, Respiratory Syncytial Virus (RSV), (human) Meta pneumovirus (MPV), Coronavirus, Herpes virus, Measles virus, Rotavirus, Calicivirus, Astrovirus and Cytomegalovirus. Most preferably the composition comprising an immunoglobulin (or Ig mixture) having respiratory syncytial virus neutralizing activity and/or an immunoglobulin (or Ig mixture) having rotavirus neutralizing activity.

Preferably the immunoglobulin is obtained or obtainable from milk and/or colostrum from hyperimmunized mammals, preferably hyperimmunized farm animals, most preferably hyperimmunized cows. Preferably the immunoglobulin is obtained or obtainable from milk from hyperimmunized cows. Methods for obtaining these immunoglobulins from a hyperimmunised mammal are well known to the skilled person and are for example described in GB1573995. The immunoglobulin used in the present invention is preferably an immunoglobulin mixture obtainable from hyperimmunized mammals. The immunoglobulin mixture from hyperimmunized animals can be differentiated from immunoglobulin mixtures from non-hyperimmunized mammals, because these immunoglobulin mixtures have a higher content of immunoglobulin directed to a specific microorganism, e.g. virus, compared to immunoglobulin mixtures obtained from normal milk. The immunoglobulin is preferably obtainable or obtained from farm animals hyperimmunized with a respiratory virus antigen and/or intestinal virus antigen, most preferably with both a respiratory virus antigen and intestinal virus antigen. The colostrum and the milk of these cows contain immunoglobulin with respiratory virus neutralizing activity and immunoglobulin with intestinal virus neutralizing activity. The immunoglobulin is preferably obtainable or obtained from farm animals hyperimmunized with a respiratory syncytial virus antigen and/or rotavirus antigen, most preferably with both a respiratory syncytial virus antigen and rotavirus antigen. In an alternative embodiment the composition contains a mixture of milks and/or colostrums, wherein at least one milk or colostrum contains immunoglobulin (or Ig mixtures) having neutralizing activity against one or more viruses that infect the respiratory tract and at least one milk or colostrum which contains an immunoglobulin having neutralizing activity against one or more viruses that infect the intestinal tract. Hence, the present composition may be obtained from the colostrum or milk of different animals, one set of animals producing immunoglobulin against one or more respiratory viruses and another set of animals producing immunoglobulin against one or more intestinal viruses.

The immunoglobulin is preferably at least one or more (mixtures) selected from the group consisting of IgM, IgY, IgG and IgA, most preferably IgG and/or IgA. Preferably the present composition contains IgG and IgA. Both classes are effective in preventing the infection of epithelial cells by pathogenic microorganisms, and both are found in colostrum and milk. Avian IgY is also proven to be effective in preventing the infection of epithelial cells by pathogenic microorganisms. Preferably the present composition contains milk derived immunoglobulin(s), wherein said milk is derived from hyperimmunised cows. Hence preferably the weight ratio IgG/IgA is between 1 and 100.

The immunoglobulin is preferably obtained from at least one dairy source selected from the group consisting of colostrum or milk products, preferably fresh milk, fresh dairy products, microfiltered milks with extended shelf life, whole colostrum powder, skim colostrum powder, milk powder, colostrum protein concentrate, milk protein concentrate milk protein isolate, colostrum protein isolate whey protein concentrate and whey protein isolate.

An infant receiving human breast milk as a substantial part of their diet receives approximately 0.2 g to 2 g immunoglobulin per day. The present method preferably comprises administering between 0.05 gram immunoglobulin per kg body weight and 2 gram immunoglobulin per kg body weight per day, more preferably between 0.1 grams/kg body weight and 1 grams/kg body weight immunoglobulin per day.

The present composition, particularly the present infant nutrition, contains between 0.25 wt. % and 5 wt. % immunoglobulin based on dry weight of the present composition.

The present composition preferably contains at least 1 wt. % immunoglobulin(s) having respiratory syncytial virus neutralizing activity based on total weight of immunoglobulin, preferably at least 2 wt. %, even more preferably at least 2.5 wt %. Preferably not more than 90 wt. %. The present composition preferably contains at least 1 wt. % immunoglobulin(s) having rotavirus neutralizing activity based on total weight of immunoglobulin, preferably at least 2 wt. %, even more preferably at least 2.5 wt %. Preferably not more than 90 wt. %.

The weight ratio GAL-oligo:immunoglobulin in the present composition is preferably between 0.01 and 100, more preferably between 0.1 and 10.

The present composition preferably provides 0.1 to 30 g of immunoglobulin(s) per day. When the composition is administered to infant, it preferably provides 0.2 to 5 g of immunoglobulin per day. When the composition is administered to adults it preferably provides 0.5 to 15 g immunoglobulin per day.

In a further preferred embodiment the present composition comprises an immunoglubolin having neutralizing activity against one or more pathogenic microorganisms selected from the group consisting of *Helicobacter pylori*, Enterotoxigenic *Escherichia coli* (ETEC) and shigella.

Digestible Galactose Saccharide

The present composition preferably comprises digestible carbohydrate containing digestible galactose saccharide. The composition contains at least 5 wt. % digestible galactose saccharide based on total dry weight of the composition, said saccharide being selected from the group consisting of galactose and digestible galactose containing saccharide containing at least two terminal saccharide units, wherein at least one terminal saccharide unit is selected from the group consisting of glucose and galactose; and at least one terminal saccharide is selected from the group consisting of galactose and fucose. The preferred composition used in the present method contains at least 5 wt % digestible galactose saccharide based on total dry weight of the present composition, preferably at least 10 wt. %, even more preferably at least 25 wt. %.

The term "digestible galactose saccharide" as used in the present invention refers to mono-, di-, tri- or polysaccharides which are digested in the intestine of normal healthy human by the action of acids or digestive enzymes present in the human upper digestive tract (small intestine and stomach). Preferably lactose is used in the present method.

Preferably the digestible galactose saccharide is lactose. Preferably at least 50 wt % of the carbohydrate of the composition used in the present method is lactose, preferably at least 75 wt. %, even more preferably at least 90 wt. %. The term carbohydrate as used herein refers to digestible carbohydrate, as is common practice. The composition used in the present method preferably contains at least 10 wt % lactose saccharide based on total dry weight of the present composition, preferably at least 25 wt. %, even more preferably at least 40 wt. %, most preferably at least 50 wt. %. In order to provide optimal nutrition to an infant, i.e. a composition which is highly similar to human milk, the present method preferably comprises the administration of a composition comprising between 40 and 60 wt. % lactose based on total dry weight of the composition.

In a further preferred embodiment the present invention relates to the administration of about 2 to 50 grams lactose per serving, preferably about 10 to 25 grams lactose per serving. A serving is preferably between 5 and 500 ml, more preferably between 100 and 300 ml.

The weight ratio digestible galactose saccharide:galactose containing indigestible oligosaccharide is preferably above 1, more preferably above 5, even more preferably above 10. The ratio is preferably below 1000, more preferably below 100.

Combinations of Oligosaccharides

In a particularly preferred embodiment the present method comprises the administration of the present GAL-oligo and a second indigestible oligosaccharides selected from the group consisting of indigestible dextrins, xylooligosaccharides, arabinooligosaccharides, glucooligosaccharides, mannooligo-saccharides, fucooligosaccharides fructans—Levan-type (β-D-(2→6)-fructofuranosyl)$_n$ α-D-glucopyranoside) and fructans—Inulin-type (β-D-((2→1)-fructofuranosyl)$_n$ α-D-glucopyranoside). Preferably the second oligosaccharide is selected from the group consisting of inulin, hydrolysed inulin and fructooligosaccharides.

The present composition preferably comprises between 0.5 and 12 grams of the second indigestible oligosaccharide, more preferably between 1 and 8 grams of the second indigestible oligosaccharide per 100 gram dry weight of the present composition. The DP of the second oligosaccharide is preferably below 40, even more preferably between 10 and 30.

Optimally, the present composition comprises between 1 and 12 grams water-soluble indigestible oligosaccharides in total (i.e. with or without a second, third, etc water-soluble indigestible oligosaccharide) per 100 gram dry weight of the present composition, more preferably between 2 and 9 grams in total.

Preferably the weight ratios:
a. (oligosaccharides with DP 2 to 5):(oligosaccharides with DP 6 to 9); and
b. (oligosaccharides with DP 10 to 60):(oligosaccharides with DP 6 to 9) are both above 1.

Preferably both weight ratios are above 2, even more preferably above 5.

The present method preferably comprises the administration of 0.5 to 10 gram transgalactooligosaccharides with DP between 1 and 10 per 100 gram dry weight of the composition, more preferably between 2 and 5 gram. The present invention preferably comprises 0.5 to 10 gram fructopolysaccharide with DP between 15 and 40 per 100 gram dry weight of the composition, more preferably between 1 and 5 gram. The term "fructopolysaccharide" refers to an indigestible polysaccharide carbohydrate comprising a chain of at least 10 β-linked fructose units.

Acid Oligosaccharides

In a further preferred embodiment the second indigestible oligosaccharide is an acid oligosaccharide. The term acid oligosaccharide refers to oligosaccharides comprising at least one acidic group selected from the group consisting of N-acetylneuraminic acid, N-glycoloylneuraminic acid, free or esterified carboxylic acid, sulfuric acid group and phosphoric acid group. The acid oligosaccharide preferably is a polyhexose. Preferably, at least one of the aforementioned acid groups is situated at the terminal hexose unit of the acid oligosaccharide. Preferably the acid oligosaccharide contains a carboxylic acid at the terminal hexose unit, wherein said carboxylic acid group may be free or esterified. Methods for the manufacture of esterified pectin hydrolysates that can be suitably used in the present method and composition are provided in WO 01/60378 and/or WO02/42484, which are hereby incorporated by reference.

Preferably, the acid oligosaccharide has one, preferably two, terminal uronic acid units, which may be free or esterified. Preferably the terminal uronic acid unit is selected from the group consisting of galacturonic acid, glucuronic acid, guluronic acid, iduronic acid, mannuronic acid, riburonic acid and alturonic acid. These units may be free or esterified. In an even more preferred embodiment, the terminal hexose unit has a double bond, which is preferably situated between the $C_4$ and $C_5$ position of the terminal hexose unit. Preferably one of the terminal hexose units comprises the double bond. The terminal hexose (e.g. uronic acid) preferably has a structure according to FIG. 1.

FIG. 1: Preferred terminal hexose acid group

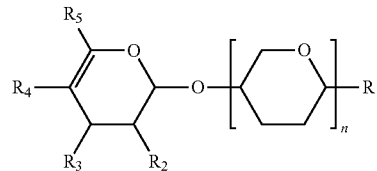

wherein;

R is preferably selected from the group consisting of hydrogen, hydroxy or acid group, preferably hydroxy (see above); and at least one selected from the group consisting of $R_2, R_3, R_4$ and $R_5$ represents N-acetylneuraminic acid, N-glycoloylneuraminic acid, free or esterified carboxylic acid, sulfuric acid group and phosphoric acid group, and the remaining of $R_2, R_3, R_4$ and $R_5$ representing hydroxy and/or hydrogen. Preferably one selected from the group consisting of $R_2, R_3, R_4$ and $R_5$ represents N-acetylneuraminic acid, N-glycoloylneuraminic acid, free or esterified carboxylic acid, sulfuric acid group and phosphoric acid group, and the remaining of $R_2, R_3, R_4$ and $R_5$ represent hydroxy and/or hydrogen. Even more preferably one selected from the group consisting of $R_2, R_3, R_4$ and $R_5$ represents free or esterified carboxylic acid and the remaining of $R_2, R_3, R_4$ and $R_5$ represent hydroxy and/or hydrogen; and n is an integer and refers to a number of hexose units (see also Degree of Polymerisation, below), which may be any hexose unit. Suitably n is an integer between 1-5000 representing the number of hexose units said hexose units preferably being uronic acid, even more preferably being galacturonic acid units. The carboxylic acid groups on these units may be free or (partly) esterified, and are preferably at least partly methylated.

Most preferably, $R_2$ and $R_3$ represent hydroxy, $R_4$ represent hydrogen and $R_5$ represents free or esterified carboxylic acid.

The acid oligosaccharide as used in the present method has a degree of polymerisation (DP) between 1 and 5000, preferably between 1 and 1000, more preferably between 2 and 250, even more preferably between 2 and 50, most preferably between 2 and 10. If a mixture of acid oligosaccharides with different degrees of polymerisation is used, the average DP of the acid oligosaccharide mixture is preferably between 2 and 1000, more preferably between 3 and 250, even more preferably between 3 and 50.

The acid oligosaccharides are preferably characterised by a degree of methoxylation above 20%, preferably above 50% even more preferably above 70%. Preferably the acid oligosaccharides have a degree of methylation above 20%, preferably above 50% even more preferably above 70%.

The acid oligosaccharide is preferably administered in an amount of between 10 mg and 100 gram per day, preferably between 100 mg and 50 grams per day, even more between 0.5 and 20 gram per day Respiratory and Intestinal Tract Infections The present invention provides a method for the treatment and/or prevention of respiratory tract infection and/or intestinal tract infections. The most common and serious respiratory and intestinal infections in infants and young children are typically caused by viral infection, however the invention is also suitable for treating and/or prevention infection by other pathogenic micro-organisms, such as but not limited to pathogenic bacteria, protozoa, parasites, prions, fungi, etc. "Pathogenic microorganisms" refer herein to microscopic or submicroscopic organisms or agents, including viruses and prions, which are capable of causing disease in humans. In a preferred embodiment the present method provides a method for the treatment and/or prevention of respiratory tract infection caused by Myxovirus, Orthomyxokvirus, Rhinovirus, Echoviruses, Coxsackieviruses, Adenovirus, Parainfluenzavirus, Respiratory Syncytial virus (RSV), (human) Meta pneumovirus (MPV), Coronavirus, Herpes virus, Measles virus, Cytomegalovirus, Histoplasma capsulatum, Coccidioides immitis, Blastomyces dermatitidis, Cryptococcus Aspergillus, Mucorales. The present method is particularly suitable for the treatment and/or prevention of respiratory syncytial virus infection and/or rotavirus infection.

In a preferred embodiment, the present method relates to the treatment and/or prevention of respiratory tract infection disease, preferably selected from the group consisting of tuberculosis, bronchitis, bronciolitis, tracheitis, pneumonia, sinusinitis, rhinitis, severe acute respiratory syndrome (SARS), croup epiglottitis, histoplasmosis, coccidioidomycosis, blastomycosis, cryptococcosis, aspergillosis, mucormycosis, lung abcess and otitis media. In a particularly preferred embodiment the invention provides a method for the treatment and/or prevention of viral pneumonia and/or bronchitis. The present method is also suitable for the treatment and/or prevention of symptoms of respiratory tract infection selected from the group consisting of irritation in the lungs, congestion in the lungs, excessive mucus production, breathlessness (i.e. difficulty with breathing), particularly breathlessness. The present method is also suitable for the treatment and/or prevention of asthma.

In a further preferred embodiment the present invention provides a method for the treatment and/or prevention of intestinal tract infections, particularly gastroenteritis, more preferably viral gastroenteritis. The present method is also suitable for the treatment and/or prevention of symptoms and sequelae of viral gastroenteritis selected from the group consisting watery diarrhea, vomiting, fever, chills and abdominal pain. The present method is also suitable for the treatment and/or prevention of more serious long-term complications such as lactose malabsorption, carbohydrate intolerance, early onset of protein intolerance and increased susceptibility to other infections.

By preventing initial infection of the intestinal and respiratory tract by pathogens that cause systemic disease, the invention can also play a role in the prevention of systemic disease including herpes simplex type I and II.

Treatment Group

The present method is particularly suitable for treatment and/or prevention of respiratory and intestinal infections in humans, preferably (healthy) children with the age between 0 and 10 years, preferably infants with the age between 0 and 4 years, and more preferably infants under 1 year of age. The present method can be advantageously used for the treatment and/or prevention of the above mentioned disease, infection and symptoms in premature infants (an infant born before 37 weeks gestation). Infants and young children at high risk due to other health complications, or due to their environment can also be suitably treated.

The present method is particularly suitable for the treatment and/or prevention of respiratory and/or intestinal infections in immunocompromised mammalian subjects, preferably elderly (human above the age of about 60), subjects infected with human immunodeficiency virus (HIV), subjects suffering from one or more of the following diseases: nephrotic syndrome, multiple myeloma, lymphoma, Hodgkin's disease, subjects which have undergone organ transplantation, subjects with chronic illnesses of the hart, kidney or lungs (especially chronic obstructive pulmonary disease (COPD), lung emphysema, sarcoidosis, cystic fybrosis, bronchiectasis, lung cancer, atelectasis, respiratory failure, occupational lung diseases, asthma), diabetes and alcoholism. The present method is advantageously used for the treatment and/or prevention of patients with COPD, HIV infection and/or diabetes, as these patients are often weakened by the disease.

In a further preferred embodiment, the present method comprises the administration of the present composition to humans, mostly hospitalized patients, that are on a ventilator or artificial breathing machine, or in the intensive care unit, as these patients are particularly vulnerable for viral infections.

An aspect of the present invention therefore is the prevention and/or reduction of occurrence and severity of a range of illness which would ordinarily be expected to result from infection of the intestinal tract. An aspect of the present invention is to combine the immune stimulating effects of indigestible oligosaccharides with immunoglobulin that can help prevent the initial ingress and infection by pathogens which cause systemic illness other than respiratory or intestinal illness.

Nutritional Formula

Drug treatment of respiratory tract infection in infants with the age between 0 and 4 is often cumbersome because many of the medicaments have to be administered via the pulmonary route. There are no effective vaccines available to prevent respiratory disease in this age group. Prevention by means of injectable monoclonal antibodies is invasive, expensive and only partly effective. The present invention provides a method for treatment and/or prevention of respiratory infections comprising orally administering a nutritional composition. Hence, the present method also overcomes the problem of pulmonary or intramuscular administration.

The nutritional composition suitable for use in the present method preferably contains between 10 and 60 en % lipid, between 5 and 50 en % protein, between 15 and 90 en % carbohydrate. More preferably the nutritional composition contains between 7.5 to 12.5 energy % protein; 40 to 55 energy % carbohydrates; and 35 to 50 energy % fat. (en % is short for energy percentage and represents the relative amount each constituent contributes to the total caloric value of the preparation).

The nutritional composition preferably also contains at least one long chain polyunsaturated fatty acid (LC-PUFA) preferably selected from the group consisting of eicosapentaenoic acid (EPA, n-3), docosahexaenoic acid (DHA, n-3) and arachidonic acid (AA, n-6), as these further reduce the respiratory tract infections and/or symptoms thereof. Preferably the present composition contains AA and DHA, even more preferably AA, DHA and EPA. The present combination of indigestible oligosaccharide(s) and LC-PUFA acts synergistically.

Preferably the present composition comprises at least 0.1 wt. %, preferably at least 0.25 wt %, more preferably at least 0.5 wt. %, even more preferably at least 0.75 wt. % LC-PUFA with 20 and 22 carbon atoms of the total fat content. The content of LC-PUFA with 20 and 22 carbon atoms in the present composition, preferably does not exceed 15 wt. % of the total fat content, preferably does not exceed 10 wt. %, even more preferably does not exceed 5 wt. % of the total fat content.

The EPA content preferably does not exceed 15 wt. % of the total fat, more preferably does not exceed 5 wt. %, most preferably does not exceed 1 wt. %, but is preferably at least 0.05 wt %, more preferably at least 0.1 wt. % of the total fat. The DHA content preferably does not exceed 10 wt. %, more preferably does not exceed 5 wt. %, most preferably does not exceed 1 wt. %, but is at least 0.1 wt % of the total fat. The present composition preferably comprises at least 0.1 wt. % AA, even more preferably at least 0.25 wt. % AA, most preferably at least 0.5 wt. % AA based on total fat. The AA content preferably does not exceed 5 wt. %, more preferably does not exceed 1 wt. % of the total fat.

Composition suitable for administration to adults may comprise increased amounts of LC-PUFA. The EPA content in this case preferably does not exceed 15 wt. % of the total fat, more preferably does not exceed 10 wt. %, but is preferably at least 0.05 wt %, more preferably at least 0.1 wt. % of the total fat. The DHA content preferably does not exceed 15 wt. %, more preferably does not exceed 10 wt. %, but is at least 0.1 wt % of the total fat. The present composition preferably comprises at least 0.1 wt. % AA, even more preferably at least 0.25 wt. % AA, most preferably at least 0.5 wt. % AA based on total fat. The AA content preferably does not exceed 15 wt. %, more preferably does not exceed 10 wt. % of the total fat.

The present method does not include a method comprising the administration of a composition consisting of human milk. Hence, preferably the present method includes the administration of a composition comprising a substance of non-human origin which is preferably a nutritional substance suitable for oral administration to a human, more preferably a fiber carbohydrate, fat and/or protein of non-human origin, preferably from plant, animal, bacterial or synthetic origin.

Pharmaceutical Formula

The present invention provides a method for treatment and/or prevention of respiratory and/or intestinal infections comprising orally administering a pharmaceutical composition with indigestible oligosaccharides and immunoglobulin. Preferred pharmaceutical formulations can be in liquid or solid form. Liquid form products can include immunoglobulin that has been derived from colostrum, milk or egg yolk by a number of methods to remove contaminating bacteria and extend shelf life. A preferred method for removing bacteria is by microfiltration. Solid form pharmaceutical compositions include powders for reconstitution, tablets, chewable tablets and capsules. A person skilled in the art can formulate products including the invention to deliver the active ingredients largely intact to certain parts of the intestine.

Probiotics

In a further preferred embodiment, the present method comprises the administration of the above-described indigestible oligosaccharide(s) and/or immunoglobulins ? and a probiotic. Preferably the probiotic is selected from the group *Lactobacillus, Lactococcus, Bifidobacterium, Enterococcus, Propionibacterium, Pediococcus, Bacillus* and *Streptococcus* and more preferably from the group consisting of *Lactobacillus* and *Bifidobacterium*. The probiotic is preferably a non-pathogenic lactic acid-producing bacterium. The combination of the present indigestible oligosaccharide(s) and the probiotic bacteria acts synergistically.

EXAMPLES

Example 1

Effectiveness of Transgalactooligsaccharides in Standard Infant Formula's for Prevention of Respiratory Tract Infections in Infants of the Age Until 1 Year Method: A multicentre clinical trial was performed in Italy, including 7 centers and 56 paediatricians. At the moment breast-feeding was stopped, infants were divided into two groups. The infants in Group A (n=69) were administered Nutrilon™ 1 or 2 supplemented with oligosaccharides to a final concentration of 0.36 g transgalactooligosaccharides/100 ml (Vivinal-GOS™; Borculo Domo Ingredients, Netherlands) and 0.04 g fructopolysaccharide/100 ml (Raftiline HP™, Orafti, Tienen, Belgium). The infants in control group B (n=82) received standard Nutrilon™ 1 or 2. Nutrilon 1™ contains 45 en % carbohydrate, 8 en % protein and 47 en % fat; about 97 wt % lactose based on total carbohydrate; 7.3 gram lactose per 100 ml; about 54 gram lactose per 100 gram dry weight of the complete composition. Nutrilon 2™ contains 47 en % carbohydrate, 10 en % protein and 43 en % fat; about 96 wt % lactose based on total carbohydrate; 7.9 gram lactose per 100 ml; about 54 gram lactose per 100 gram dry weight of the complete composition.

Results: The age of the infants varied between 2 and 9 months and the infants were followed for 6 months. Both groups did not show any difference in nutritional intake. In group A a total number of 32 upper respiratory tract infection episodes was observed. In control group B a total number of 60 upper respiratory tract infection episodes was observed. Thus the incidence of upper respiratory infection episodes was significant (p<0.01) lower in group A vs group B.

Example 2

Immune Stimulatory Effect of Composition with Indigestible Galactose Containing Oligosaccharides Experimental setup: Diets comprising indigestible galactose containing oligosaccharides were tested on the delayed-type hypersensitivity (DTH) response by orally ingestion of diets containing indigestible galactose containing oligosaccharides by mice. The DTH is a parameter for Th1 immunological response and is determined by measuring the increase in ear swelling after local antigen challenge. For the DTH responses, mice were i.c. injected with 25 μl dialysed Influvac in both ears as a DTH challenge.

Neutral oligosaccharide mixture (GF) containing galactooligosaccharides (GOS) (Vivinal-GOS™ (Borculo Domo Ingredients, Netherlands) and fructooligosaccharides (FOS) (Raftiline HP™, Orafti, Tienen, Belgium) were used in a weight ratio GOS:FOS of 9:1. Diets containing 1, 2.5 and 5 wt. % GF based on total weight of the diet were tested.

Results: Administering diets with 1 or 2.5 wt. % GF induces a statistically significant increase in the DTH (see Table 1). These results are indicative for the immunestimulatory effects of indigestible galactose containing oligosaccharides, which may even be enforced by including of fructopolysaccharides.

TABLE 1

| Wt. % oligosaccharides in diet | DTH response (%) |
| --- | --- |
| 0 (control) | 100 |
| 1 wt % GF | 132* |
| 2.5 wt % GF | 129* |

*indicates significantly different (P < 0.05) from control

Example 3

Anti-Infective Composition

Infant formula with 40 en % lipid, 11 en % protein and 49 en % carbohydrate containing:
a. milk obtained from cows hyperimmunized with rotavirus antigen and *E. coli* antigen and thus containing immunoglobulin (IgG) having rotavirus neutralizing activity, and activity against *E. coli*.
b. Transgalactoligosaccharides (Vivinal™ (Borculo Domo Ingredients, Netherlands).)
c. Lactose Example 4

Anti-Infective Composition

Infant formula with 40 en % lipid, 11 en % protein and 49 en % carbohydrate containing:
a. milk obtained from cows hyperimmunized with rotavirus antigen and respiratory syncytial virus antigen, and thus containing immunoglobulin (IgG) having rotavirus neutralizing activity and immunoglobulin (IgG) having respiratory syncytial virus neutralizing activity.
b. Transgalactoligosaccharides (Vivinal™ (Borculo Domo Ingredients, Netherlands).)
c. Lactose

The invention claimed is:

1. A method of reducing the incidence of upper respiratory tract infection episodes comprising administering to an infant mammal in need thereof a liquid infant formula composition consisting of:
    (a) 0.5-10 grams transgalactooligosaccharide per 100 grams dry weight of the composition,
    (b) 0.5-10 grams fructopolysaccharide per 100 grams dry weight of the composition,
    (c) optionally, indigestible dextrins, xylooligosaccharides, arabinooligosaccharides, glucooligosaccharides, mannooligosaccharides, fucooligosaccharides, fructans, fructooligosaccharide, hydrolysed inulin, inulin or lactose, and
    (d) optionally, a long chain polyunsaturated fatty acid (LC-PUFA),
    wherein, as a percentage of the total caloric value of the composition, (i) 35-50% energy is derived from fat; (ii) 7.5-12.5% energy is derived from protein; and 40-55% energy is derived from carbohydrate; and
    wherein the composition is in the form of a liquid and does not comprise human milk.

2. The method according to claim 1, wherein the mammal is a human.

3. The method according to claim 1, wherein the composition is administered orally.

4. The method according to claim 1, wherein the fat, carbohydrate, or protein is of plant, non-human animal, bacterial, or synthetic origin.

5. The method according to claim 1, wherein the composition consists of
    (a) 2-5 grams transgalactooligosaccharide per 100 grams dry weight of the composition, and
    (b) 1-5 grams fructopolysaccharide per 100 grams dry weight of the composition,
    wherein the composition is in the form of a liquid and does not comprise human milk.

6. The method according to claim 1, wherein the composition consists of:
    (a) 0.5-10 grams transgalactooligosaccharide per 100 grams dry weight of the composition,
    (b) 0.5-10 grams fructopolysaccharide per 100 grams dry weight of the composition,
    (c) a fructan, fructooligosaccharide, a hydrolysed inulin or an inulin, and
    (d) optionally, a long chain polyunsaturated fatty acid (LC-PUFA),
    wherein, as a percentage of the total caloric value of the composition, (i) 35-50% energy is derived from fat; (ii) 7.5-12.5% energy is derived from protein; and 40-55% energy is derived from carbohydrate; and
    wherein the composition is in the form of a liquid and does not comprise human milk.

7. The method according to claim 1, wherein at least 50%, by weight, of the carbohydrate of the composition is lactose.

8. The method according to claim 1, wherein the LC-PUFA is selected from the group consisting of eicosapentaenoic acid (EPA, n-3), docosahexaenoic acid (DHA, n-3) and arachidonic acid (AA, n-6).

9. A method of reducing the incidence of upper respiratory tract infection episodes comprising administering to an infant mammal in need thereof a liquid infant formula composition consisting of:
  (a) 0.5-10 grams transgalactooligosaccharide per 100 grams dry weight of the composition,
  (b) 0.5-10 grams fructopolysaccharide per 100 grams dry weight of the composition,
  (c) optionally, indigestible dextrins, xylooligosaccharides, arabinooligosaccharides, glucooligosaccharides, mannooligosaccharides, fucooligosaccharides, fructans, fructooligosaccharide, hydrolysed inulin or inulin, and
  (d) optionally, a long chain polyunsaturated fatty acid (LC-PUFA),
wherein the composition is in the form of a liquid and does not comprise human milk.

* * * * *